United States Patent [19]
Broun et al.

[11] Patent Number: 5,965,793
[45] Date of Patent: Oct. 12, 1999

[54] STRONG EARLY SEED-SPECIFIC GENE REGULATORY REGION

[75] Inventors: Pierre Broun, Burlingame; Chris Somerville, Portola Valley, both of Calif.

[73] Assignees: Monsanto Company, Inc., St. Louis, Mo.; Carnegie Institution of Washington, Washington, D.C.

[21] Appl. No.: 08/898,038

[22] Filed: Jul. 18, 1997

Related U.S. Application Data

[63] Continuation-in-part of application No. 08/530,862, Sep. 20, 1995, application No. 08/597,313, Feb. 6, 1996, and application No. PCT/US97/02187, Feb. 6, 1997.

[51] Int. Cl.$^6$ ............................ C12N 15/29; C12N 15/82; C12N 5/04; A01H 5/00
[52] U.S. Cl. ...................... 800/287; 536/24.1; 536/23.1; 536/23.6; 435/69.1; 435/468; 435/410; 435/419; 435/318; 435/320.1; 800/281; 800/298; 800/306
[58] Field of Search .................................. 536/24.1, 23.1, 536/23.6; 800/287, 295, 278, 306, 281; 435/69.1, 468, 410, 419, 418, 320.1

[56] References Cited

U.S. PATENT DOCUMENTS

| | | |
|---|---|---|
| 5,057,419 | 10/1991 | Martin et al. . |
| 5,443,974 | 8/1995 | Hitz et al. . |
| 5,475,099 | 12/1995 | Knauf et al. . |
| 5,487,991 | 1/1996 | Vandekerckhove et al. . |
| 5,530,186 | 6/1996 | Hitz et al. . |

OTHER PUBLICATIONS

Van De Loo et al., "An Oleate 12–Hydroxylase From Ricinus Communis L. Is A Fatty Acyl Desaturase Homolog", Proc. Natl. Acad. Sci., vol. 92, 1995, pp. 6743–6747.
Okuley et al., "Arabidopsis FAD2 Gene Encodes The Enzyme That Is Essential For Polyunsaturated Lipid Synthesis", The Plant Cell., vol. 6, 1994, pp. 147–158.
Broun et al., Accumulation of Ricinoleic, Lesquerolic, and Densipolic Acids in Seeds of Transgenic Arabidopis Plants That Express a Fatty Acyl Hydroxylase cDNA from Castor Bean, Plant Physiol. (1997) 113:933–942.
Broun et al., A bifunctional oleate 12–hydroxylase: desaturase from Lesquerella fendleri, The Plant Journal (1998) 13(2), 201–210.
Arondel et al. Science, 258: 1353–1355 (1992).
Carlson et al, J. Am. Oil Chem. Soc., 67:438–442 (1990).
Gibson et al., Plant Physiol., 106: 1615–1621 (1994).
Jones et al., Transgenic Res., 1:285–297 (1992).
Matzke et al., Plant Physiol. 107: 679–685, (1995).
Topfer et al., Science 268: 681–686+P (1995).
van de Loo et al. Proc. Natl. Acad. Sci. USA, 92:6743–6747 (1995).
Kim et al. Plant Molecular Biology. 1994, vol. 24: 105–117.
Napoli et al. The Plant Cell. 1989. vol. 2: 278–289.

*Primary Examiner*—Elizabeth F. McElwain
*Assistant Examiner*—Ousama M-Faiz Zaghmount
*Attorney, Agent, or Firm*—Pillsbury Madison & Sutro LLP

[57] ABSTRACT

Nucleic acid sequences and methods for their use are described which provide for early seed-specific transcription, in order to modulate or modify expression of foreign or endogenous genes in seeds, particularly embryo cells. The method finds particular use in conjunction with modifying fatty acid production in seed tissue.

20 Claims, 6 Drawing Sheets

FIG. 3A

```
         10          20          30          40          50
AAGCTTTTGA GCTCATCAGT TACTCAGGAA GATTAAGTCT TTGCTTGTTG
HindIII
         60          70          80          90         100
TCTGATTTTC TTTAAATACA TGAAGGATCG GTTATGAATC TTCTTTTTTT
        110         120         130         140         150
GTGTTTTGGG ATTATGAAGC TGTCTTTGGA TATTAGTTGC GGTTATTAGC
        160         170         180         190         200
ATGCTTCTCT TTTGTGTTTT GGGGATTATG AAGCAGGGTC TGTCTATGTA
        210         220         230         240         250
ATGCATTTTG TTTGAAAACT CAGCTAATGC TAATGCAATT TCTTTTGAAA
        260         270         280         290         300
CCTTTGTTAT GTTTTCGAAA ATATTGAATA NGTTCTGTTA TGGATTTATT
        310         320         330         340         350
TGCAAAAGCC ATTGATTAAA TCAAACATTA CATAAGAACA ACATTCATTA
        360         370         380         390         400
TTAACTAATT AGAGATGCAA AACACAACAT TACATACAAC ATCAGTGACT
        410         420         430         440         450
AATTATTGAG ACAAAACAAC ATCACATACA CAAACATTCA TCTCATACAT
        460         470         480         490         500
CACTTAGAGA GACACAAAAA GCAACCAAAC ACAACTATTC CGGCAACAAC
        510         520         530         540         550
AATTAGCTTC ATACGTTTTG CTTCTCCTTT CAAGCCTTCA ATCATCTTCT
        560         570         580         590         600
CACAGCCACG AATCTGAGCC TTCAATAATA ACATTTCTTC ATCGTGACAC
        610         620         630         640         650
TTCTCACGGT TATGAATGTA AGCCTTTATG TCCTCTACTT CTTCTACTAA
        660         670         680         690         700
AGACACATCA GTCCACTTCC AGGTGTGGAA TCCTCCTCTT TTGAAATTTT
        710         720         730         740         750
TCTCACAGGT ATGGAATAAT CTACCTAGGT TTTTTGGAGT TCTTGAGGTT
        760         770         780         790         800
CTGATCACAA CACGACATCC AAATCGACAG GTCTTAGGAA AACCACGATG
        810         820         830         840         850
GTTATCATCT TCAAGCTCAC TGTCAAAAGA GAAAACGAG TTTGAAGAAG
        860         870         880         890         900
AAGAAGGCAT TATCAATTTC AGAGAATTTT GGAGAATTTT GAGAGATTGA
        910         920         930         940         950
GAATTGGGAA ATAAGAACCC TAATCCCCAA TTTATGAGAT TGAAAATATA
        960         970         980         990        1000
TCCGTTAGAG AAGAAACATA ATGCTGTGCG TTTTAATTAG AAAAAATAGA
       1010        1020        1030        1040        1050
GATGGGCTTT ATCTTTTGTT AAGAGTTTTG GCTTGGGCT TGGGTTTTTG
       1060        1070        1080        1090        1100
ATAAAAAAAT TTAATTAAAC CAAAACGACG TCGTTTGGTT TAATTGTTGT
       1110        1120        1130        1140        1150
TAAAAAAAAT TAAAACACCA AAACGACGTC GTTTTGGTGT TATTAACGGC
       1160        1170        1180        1190        1200
CTTAAAACGG ATTAAATCCA TAATCCGTCA GTCAACTAGG TTACGGATGG
       1210        1220        1230        1240        1250
TCAACGGCGT TTTTGCATAA CGGAGGCACA GTTCAGGCTT AACGGAGTGG
```

FIG. 3B

```
           1260       1270       1280       1290       1300
       ACCGAATGGC TTTTTAGGAA GTTTGTAACC GGGATTTTTT GTTTATGATG
           1310       1320       1330       1340       1350
       TATTTGTCCC CGTCGGCTAT TGTTTAGGCC GTTTTTCCTA TATATTGGAA
           1360       1370       1380       1390       1400
       ATAACTATTG TCCAGACGAG TTACTTCTCC AACATATCAA GAAATGTTAC
           1410       1420       1430       1440       1450
       AAAGAAGTGT TACAAAAATG TGTTACTAAG CCATAAAACT CAAAGCATAT
           1460       1470       1480       1490       1500
       ATCTTAGACC CTAAGCCTAA ACCCTAGAAC TTTCTAGGAC GTTTATACCT
           1510       1520       1530       1540       1550
       TGTCCTTTCT TTAGTTTCCT TTAAAGGCCT TCGTATTCAT AAGTTTTATT
           1560       1570       1580       1590       1600
       TTTGCTTAAT ACTAACACTA GAAATAATCA ACATAAACTA GGTTAAGTCG
           1610       1620       1630       1640       1650
       TGGATCTAAT TTTATTGTGA AAATGTAATT GCTTCTCTTA AGAAAAGATT
           1660       1670       1680       1690       1700
       CATAGCAAAA TATTCGCATC TTTCTTGTGA ATCATCTTTT GTTTTTGGGG
           1710       1720       1730       1740       1750
       CTATTAAAGA AAAATTGAAC TCATGAAATG GTGACAACTT TATTCTAGAG
           1760       1770       1780       1790       1800
       GTAACAGAAC AAAAATATAG GAACAACACG TGTTGTTCAT AAACTACACG
           1810       1820       1830       1840       1850
       TATAATACTC AAGAAGATGA ATCTTTATAA GAATTTAGTT TTCTCATGAA
           1860       1870       1880       1890       1900
       AACATAAAAA ATTTTGTCAA TTGAAAGTGA CAGTTGAAGC AAAGGAACAA
           1910       1920       1930       1940       1950
       AAGGATGGTT GGTGATGATG CTGAAATGAA AATGTGTCAT TCATCAAATA
           1960       1970       1980       1990       2000
       CTAAATACTA CATTACTTGT CACTGCCTAC TTCTCCTATT TCCTCCGCCA
           2010       2020       2030       2040       2050
       CCCATTTTGG ACCCACGAGC CTTCCATTTA AACCCTCTCT CGTGCTATTC
           2060       2070       2080       2090       2100
       ACCAGAAGAG AAGCCAAGAG AGAGAGAGAG AGATTGTGCT GAGGATCATT
           2110       2120       2130       2140       2150
       GTCTTCTTCA TCGTTATTAA CGTAAGTTTT TTTTGACCAC TCATATCTAA
           2160       2170       2180       2190       2200
       AATCTAGTAC ATGCAATAGA TTAATGACTG TTCCTTCTTT TGATATTTTC
           2210       2220       2230       2240       2250
       AGCTTCTTGA ATTCAAGATG GGTGCTGGTG GAAGAATAAT GGTTACCCCC
              EcoRI
           2260       2270       2280       2290       2300
       TCTTCCAAGA AATCAGAAAC TGAAGCCCTA AAACGTGGAC CATGTGAGAA
           2310       2320       2330       2340       2350
       ACCACCATTC ACTGTTAAAG ATCTGAAGAA AGCAATCCCA CAGCATTGTT
           2360       2370       2380       2390       2400
       TCAAGCGCTC TATCCCTCGT TCTTTCTCCT ACCTTCTCAC AGATATCACT
           2410       2420       2430       2440       2450
       TTAGTTTCTT GCTTCTACTA CGTTGCCACA AATTACTTCT CTCTTCTTCC
           2460       2470       2480       2490       2500
       TCAGCCTCTC TCTACTTACC TAGCTTGGCC TCTCTATTGG GTATGTCAAG
```

FIG. 3C

```
            2510       2520       2530       2540       2550
       GCTGTGTCTT AACCGGTATC TGGGTCATTG GCCATGAATG TGGTCACCAT
            2560       2570       2580       2590       2600
       GCATTCAGTG ACTATCAATG GGTAGATGAC ACTGTTGGTT TTATCTTCCA
            2610       2620       2630       2640       2650
       TTCCTTCCTT CTCGTCCCTT ACTTCTCCTG GAAATACAGT CATCGTCGTC
            2660       2670       2680       2690       2700
       ACCATTCCAA CAATGGATCT CTCGAGAAAG ATGAAGTCTT TGTCCCACCG
            2710       2720       2730       2740       2750
       AAAAAGCTG CAGTCAAATG GTATGTTAAA TACCTCAACA ACCCTCTTGG
            2760       2770       2780       2790       2800
       ACGCATTCTG GTGTTAACAG TTCAGTTTAT CCTCGGGTGG CCTTTGTATC
            2810       2820       2830       2840       2850
       TAGCCTTTAA TGTATCAGGT AGACCTTATG ATGGTTTCGC TTCACATTTC
            2860       2870       2880       2890       2900
       TTCCCTCATG CACCTATCTT TAAAGACCGA GAACGCCTCC AGATATACAT
            2910       2920       2930       2940       2950
       CTCAGATGCT GGTATTCTAG CTGTCTGTTA TGGTCTTTAC CGTTACGCTG
            2960       2970       2980       2990       3000
       CTTCACAAGG ATTGACTGCT ATGATCTGCG TCTATGGAGT ACCGCTTTTG
            3010       3020       3030       3040       3050
       ATAGTGAACT TTTTCCTTGT CTTGGTAACT TTCTTGCAGC ACACTCATCC
            3060       3070       3080       3090       3100
       TTCGTTACCT CATTATGATT CAACCGAGTG GGAATGGATT AGAGGAGCTT
            3110       3120       3130       3140       3150
       TGGTTACGGT AGACAGAGAC TATGGAATAT TGAACAAGGT GTTCCATAAC
            3160       3170       3180       3190       3200
       ATAACAGACA CACATGTGGC TCATCATCTC TTTGCAACTA TACCGCATTA
            3210       3220       3230       3240       3250
       TAACGCAATG GAAGCTACAG AGGCGATAAA GCCAATACTT GGTGATTACT
            3260       3270       3280       3290       3300
       ACCACTTCGA TGGAACACCG TGGTATGTGG CCATGTATAG GGAAGCAAAG
            3310       3320       3330       3340       3350
       GAGTGTCTCT ATGTAGAACC GGATACGGAA CGTGGGAAGA AAGGTGTCTA
            3360       3370       3380       3390       3400
       CTATTACAAC AATAAGTTAT GAGGCTGATA GGGCGAGAGA AGTGCAATTA
            3410       3420       3430       3440       3450
       TCAATCTTTT TTTCATGTTT TAGGTGTCTT GTTTAAGAAG CTATGCTTTG
            3460       3470       3480       3490       3500
       TTTCAATAAT CTCAGAGTCC ATTTAGTTGT GTTCTGGTGC ATTTTGCCTA
            3510       3520       3530       3540       3550
       GTTATGTGGT GTCGGAAGTT AGTGTTCAAA CTGCTTCCTG CTGTGCTGCC
            3560       3570       3580       3590       3600
       CAGTGAAGAA CAAGTTTACG TGTTTAAAAT ACTCGGAACG AATTGACCAC
            3610       3620       3630       3640       3650
       AANATATCCA AAACCGGCTA TCCGAATTCC ATATCCGAAA ACCGGATATC
            3660       3670
       CAAATTTCCA GAGTACTTAG
```

STRONG EARLY SEED-SPECIFIC GENE REGULATORY REGION

CROSS-REFERENCES TO RELATED APPLICATIONS

This is a continuation in-part of U.S. appln. Ser. No. 08/530,862, filed Sep. 20, 1995, pending; U.S. appln. Ser. No. 08/597,313, filed Feb. 6, 1996, pending; and application PCT/US97/02187, filed Feb. 6, 1997, designating the U.S.

GOVERNMENT RIGHTS

The invention described herein was made in the course of work under grant number DE-FG02-94ER20133 from the U.S. Department of Energy. Therefore, the U.S. Government may retain certain rights in this invention.

INTRODUCTION

1. Technical Field

A transcription regulatory region, comprising a nucleotide sequence, which promotes early seed-specific transcription of contiguous nucleotide sequences is provided.

2. Background

A large number of genes are known which are expressed only in developing seeds, or are expressed in developing seeds at much higher levels than in any other organ or tissue type. For the purposes herein, "gene expression" refers to synthesis of mRNA corresponding to a given gene. Thus, the amount of gene expression generally refers to the rate of transcription, or the rate of synthesis of the mRNA. For convenience, in the context of this invention, we have generally assumed that differences in the steady-state level of mRNA accumulation reflects differences in the rate of synthesis of the mRNA. It is understood that in some cases changes in the steady-state level of mRNA could be caused by changes in the rate of mRNA degradation. However, it is considered unlikely that manipulation of promoter sequences, as taught herein, will generally affect the rate of mRNA degradation.

Much of the information about seed-specific gene expression has been derived from studies of genes encoding storage proteins (reviewed by Bevan et al., 1993). For instance, DNA sequences that confer embryo-specific expression by the soybean conglycinin promoter in transgenic plants have been identified (Chen et al., 1988). Similarly, the storage protein napin is one of the major protein components of Brassica napus L. (oilseed rape) seeds. A 152 bp fragment from the napin promoter directed strong expression of the β-glucuronidase reporter gene in mature tobacco seeds (Stalberg et al., 1996). Thus, the sequences that direct strong seed-specific expression of storage proteins are conserved between distantly related plant species. The napin promoter has been used to control expression of genes in transgenic plants designed to produce novel fatty acids (e.g., Voelker et al., 1996). However, because storage lipid accumulation begins substantially before the maximal level of expression of the napin or other storage protein genes is reached (Post-Beittenmillar et al., 1992), the promoters of storage protein genes may not be preferred for controlling expression of genes related to storage lipid accumulation.

In the present invention, a preferred regulatory region (e.g., promoter, enhancer, silencer) for expression of genes directed toward modification of seed lipid composition, or other applications, would be derived from a gene that has a similar, or identical, temporal and tissue-specific pattern of expression to the genes that encode enzymes involved in seed storage lipid synthesis and accumulation. However, until recently, relatively few genes were known which are involved in lipid metabolism and are expressed in a seed-specific manner. The kappa hydroxylase from the Crucifer *Lesquerella fendleri* is one of the first examples of this class of genes. A promoter of the present invention normally controls the expression of the kappa hydroxylase from *L. fendleri*. Kappa hydroxylase is thought to be located in the endoplasmic reticulum where it catalyzes the introduction of a hydroxyl group into fatty acids attached to the sn-2 position of phospholipids. Since hydroxylated fatty acids are abundant in the seed storage lipids of *L. fendleri* but are not found to any appreciable extent in other organs or tissues, it seems likely that the gene is only expressed appreciably in seeds. The isolation of the kappa hydroxylase gene from *L. fendleri* was described in U.S. pat. appln. Ser. Nos. 08/530,862 and 08/597,313, and PCT/US97/02187. Evidence was presented showing that the mRNA for the kappa hydroxylase was abundant in seeds but was not detectable in vegetative tissues. Here, we demonstrate that a regulatory region in the 5' direction from the coding sequence of the *L. fendleri* kappa hydroxylase is useful as a seed-specific promoter in plant species other than *L. fendleri*. We also show that the regulatory region can be used to cause early seed-specific expression of a gene other than the kappa hydroxylase (i.e., heterologous gene expression). Regulatory regions having the desired properties described herein should also be found upstream of other plant fatty acyl hydroxylase genes isolated and identified as disclosed in the parent applications.

SUMMARY OF THE INVENTION

It is an object of the present invention to provide a transcription regulatory region for use in transgenic plants that exhibits seed-specific expression of a gene product.

It is a further object of the present invention to provide a transcription regulatory region for use in transgenic plants that exhibits an early level of expression of a gene product in developing seeds.

It is yet another object of the present invention to provide a transcription regulatory region for use in transgenic plants that exhibits high-level expression of a gene product.

Isolated nucleic acids (e.g., DNA, RNA, cDNA, cRNA) are provided that comprise a transcription regulatory region (e.g., promoter, enhancer, silencer) from a plant fatty acyl hydroxylase gene. Preferably, the plant gene is a kappa hydroxylase gene and, more preferably, the kappa hydroxylase gene is from Lesquerella. The regulatory region may comprise a nucleotide sequence from SEQ ID NO:1. The regulatory region may comprise between about 500 nucleotides to about 2000 nucleotides, and may be capable of directing expression at a high level, at an early stage of development, in a seed-specific manner, or a combination thereof. The isolated nucleic acid may further comprise a sequence encoding for the native fatty acyl hydroxylase.

Recombinant nucleic acids (e.g., DNA, RNA, cDNA, cRNA) are provided that are comprised of the isolated nucleic acid described above and an operably linked non-native sequence to be transcribed. The sequence may be from the same plant species from which the regulatory region is derived or from a different species or genera; the sequence may even be from a bacterial, fungal, or mammalian gene. Preferably, the sequence is derived from a plant gene, especially one that is involved in seed lipid metabolism or seed development. The sequence may be in the sense or antisense orientation relative to transcription.

Expression constructs (e.g., DNA, RNA, cDNA, cRNA) are provided which are employed in manipulating plant cells to provide for early and/or seed-specific transcription. In particular, transcription regulatory regions from a gene encoding a fatty acyl hydroxylase are operably linked to other than the native or homologous gene, and introduced into a plant cell host for integration into the genome to provide for early and/or seed-specific transcription. The constructs provide for modulation of expression of endogenous products as well as production of exogenous products in the seed.

Transformed host cells, transgenic plants, and transgenic seeds are provided that contain an integrated or non-integrated nucleic acid, recombinant nucleic acid, or expression construct as described above. The host cell may be of bacterial, fungal, plant, animal, or similar origin. The transgenic plant may be Arabidopsis, Brassica, cotton, soybean, safflower, sunflower, tobacco, flax, peanut, or any other dicot species in which early seed-specific gene expression is desired. The regulatory region of the invention may also be useful in controlling seed-specific expression of genes in monocotyledonous species such as wheat, maize, rice, or the like. Transgenic seeds may be derived from similar plant species. Oil may be pressed, or otherwise extracted, or other materials such as proteins, carbohydrates, polyalkanoates, or secondary metabolites may be extracted from the transgenic seed.

Kits are also provided containing a nucleic acid, recombinant nucleic acid, expression contruct, host cell, or a combination thereof with directions for the use of the aforementioned to produce a transgenic plant or seed.

BRIEF DESCRIPTION OF THE DRAWINGS

FIG. 3 shows a partial nucleotide sequence of genomic clone pLesqtot containing the promoter region and coding region of the kappa hydroxylase gene from *L. fendleri*. The clone (3670 bp of continuous nucleotide sequence, SEQ ID NO:1) encodes a 2217 bp 5' untranslated region (i.e., sequence preceding the initiating ATG codon), an 1152 bp open reading frame, and a 302 bp 3' untranslated region. The HindIII and EcoRI sites used in subcloning are indicated with double underlines. The ATG that corresponds to the first translated codon of the kappa hydroxylase is underlined.

DETAILED DESCRIPTION OF THE INVENTION

Figure 1:
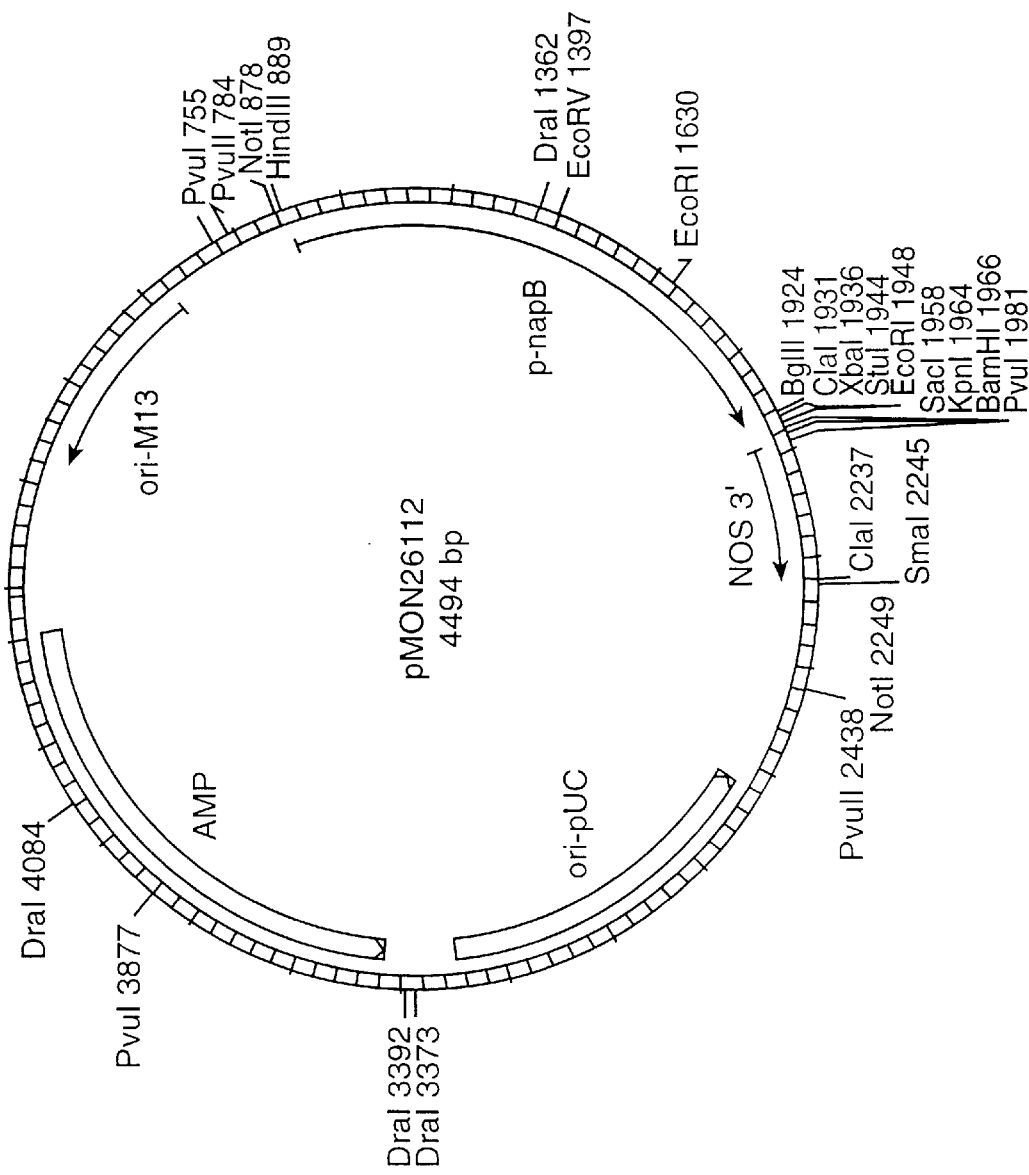
FIG. 1 is a restriction map of plasmid pMON26112.

In accordance with the subject invention, expression constructs are provided which allow for modification of transcription in seeds, particularly in embryos during seed maturation. The expression constructs comprise a regulatory region (e.g., promoter, enhancer, silencer) associated with seed formation, preferably in association with embryogenesis and seed maturation.

Downstream from and under the transcriptional regulation of the kappa hydroxylase regulatory region will be a sequence of interest which will provide for modification of the phenotype of the seed, by modulating the production of an endogenous product, as to amount, relative distribution, timing or the like, or production of an exogenous expression product to provide for a novel function or product in the seed. The construct will preferably provide for a polyadenylation and/or a termination region, so as to provide an expression cassette into which a gene may be introduced.

Conveniently, transcriptional initiation and termination regions may be provided separated in the direction of transcription by a linker or polylinker having one or a plurality of restriction sites for insertion of the gene to be under the transcription regulation of the regulatory region (s). Usually, the linker will have from 1 to 10, more usually from about 1 to 8, preferably from about 2 to 6 restriction sites. Generally, the linker will be fewer than 100 bp, frequently fewer than 60 bp and generally at least about 5 bp. For an insert generated by nucleic acid amplification, the insert may be linked to a regulatory region by techniques such as, for example, restriction enzyme digestion, direct blunt-end ligation, ligation-independent cloning (LIC), and ligation to a single 3'-overhang of a thymidine residue (U.S. Pat. No. 5,487,993).

The transcription regulatory region of this invention may be foreign, or heterologous to the host. By foreign is intended that the regulatory region is not found in the host into which the regulatory region is introduced. Of particular interest are those transcription regulatory regions associated with the seed-specific kappa hydroxylase gene, especially that of *L. fendleri*.

A transcription regulatory region may be used for varying the phenotype of seeds. Various changes in phenotype are of interest. These include modifying the fatty acid composition in seeds, that is changing the ratio and/or amounts of the various fatty acids, as to length, unsaturation, hydroxlation, epoxidation, or the like. Thus, the fatty acid composition may be varied by introducing enzymes which modify the fatty acids to produce fatty acids which are not normally found in the host plant. It may also be desirable to use the promoter of this invention to produce proteins that are directly useful in their own right, such as proteins that have catalytic properties for industrial use. Alternatively, one may provide various products from sources other than plants such as, for example, mammals, fungi, archaeabacteria, and eubacteria. Indeed, the transcriptional initiation region of this invention may be generally used to produce any protein of interest in a seed of a plant host.

An expression cassette may include in the 5'→3' direction of transcription, a transcriptional initiation region, a nucleotide sequence of interest, and a transcriptional termination region functional in plants. In many, but not all, cases the expression cassette may also include translation initiation and termination sequences (i.e. a transcriptional/translational cassette). One or more introns may also be present.

The nucleotide sequence may usually have any open reading frame encoding at least part of a peptide of interest (e.g., an enzyme), or a sequence complementary to a genomic sequence (e.g., antisense), where the genomic sequence may be an open reading frame, an intron, a non-coding leader sequence, or any other sequence where the complementary sequence will inhibit transcription, messenger RNA processing (e.g., splicing), or translation. The nucleotide sequence of interest may be synthetic, naturally derived, or a combination thereof; the nucleic acid may be purified from a natural source (e.g., bacteria), a reaction mixture comprising template and a polymerase (producing DNA, cDNA or cRNA), or chemical synthesis.

In preparing the expression cassette, the various nucleotide fragments may be manipulated, so as to provide for nucleotide sequences in the proper orientation and, as appropriate, in the proper reading frame. Towards this end, adapters or linkers may be employed to join the nucleotide fragments or other manipulations may be involved to provide for convenient restriction sites, removal of superfluous nucleotides, removal of restriction sites, or the like. For this purpose, in vitro mutagenesis, primer repair, restriction, annealing, resection, ligation, or the like may be employed, where insertions, deletions, inversions, or substitutions (e.g., transition, transversion), may be involved.

The termination region which is employed will be primarily chosen for convenience, since the termination regions appear to be relatively interchangeable. The termination region may be native to the transcriptional initiation region, may be native to the nucleotide sequence of interest, or may be derived from another source. Convenient termination regions are available from the Ti-plasmid of *A. tumefaciens*, such as the octopine synthase and nopaline synthase termination regions.

The nucleic acids and constructs of the invention may further comprise sequences that permit propagation and selection of the constructs in a foreign host. Optionally, an origin of replication and a selectable marker may be included in the nucleic acid or construct. The origin of replication would preferably be derived from a microbe (e.g., bacteria, fungi), but may also be derived from a DNA or RNA virus. The selectable marker may be operative in prokaryotes and/or eukaryotes, and confer resistance to antibiotics such as, for example: ampicillin, hygromycin, kanamycin, neomycin, puromycin, tetracycline, or the like.

By appropriate manipulations, such as restriction, digesting back or filling in overhangs to provide blunt ends, ligation of linkers, or the like, complementary or flush ends of the fragments can be provided for joining and ligation.

In carrying out the various steps, cloning is employed, so as to amplify the amount of DNA and to allow for analyzing the DNA to ensure that the gene manipulations have occurred in a proper manner. A wide variety of cloning vectors are available, where the cloning vector includes a replication system functional in *E. coli* and a marker which allows for selection of the transformed cells. Illustrative vectors include pBR332, the pUC series, the M13 mp series, pACYC184, etc. Thus, the sequence may be inserted into the vector at an appropriate restriction site(s), the resulting plasmid used to transform the *E. coli* host, the *E. coli* grown in an appropriate nutrient medium, the cells harvested and lysed, and the plasmid recovered. Analysis may involve sequence analysis, restriction analysis, induction of expression, electrophoresis, or the like. After each manipulation, the DNA sequence to be used in the final construct may be restricted and joined to the next sequence, where each of the partial constructs may be cloned in the same or different plasmids.

Depending upon the manner of introduction of the transcription construct into the host plant, other nucleotide sequences may be required. For example, when using the Ti- or Ri-plasmid for transformation of plant cells, as described below, at least the right border and frequently both the right and left borders of the T-DNA of the Ti- and Ri-plasmids will be joined as flanking regions to the transcription construct. The use of T-DNA for transformation of plant cells has received extensive study and is amply described in Fraley et al. (1986) and Lindsey (1996).

A variety of techniques are available for the introduction of nucleic acids into a plant cell host. These techniques include transformation with Ti-DNA employing *A. tumefaciens* or *A. rhizogenes* as the transforming agent, protoplast fusion, injection, electroporation, etc. (reviewed by Lindsey, 1996). For transformation with Arobacterium, plasmids can be prepared in *E. coli* which plasmids contain DNA homologous with the Ti-plasmid, particularly T-DNA. The plasmid may or may not be capable of replication in Arobacterium, that is, it may or may not have a broad spectrum prokaryotic replication system (e.g., RK290) depending in part upon whether the transcription construct is to be integrated into the Ti-plasmid or be retained on an independent plasmid. By means of a helper plasmid, the transcription construct may be transferred to *A. tumefaciens* and the resulting transformed organism used for transforming plant cells.

Conveniently, explants may be cultivated with *A. tumefaciens* or *A. rhizogenes* to allow for transfer of the expression cassette to the plant cells, the plant cells dispersed in an appropriate selective medium for selection, grown to callus, shoots grown and plantlets regenerated from the shoots by growing in rooting medium. The Agrobacterium host will contain a plasmid having the vir genes necessary for transfer of the T-DNA to the plant cells and may or may not have T-DNA. For injection and electroporation, disarmed Ti-plasmids (lacking the tumor genes, particularly the T-DNA region) may be used to introduce genes into the plant cell.

The cells which have been transformed may be grown into plants and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

As a host cell, any plant variety may be employed which provides a seed of interest. Thus, for the most part, plants will be chosen where a seed-specific product of interest is involved. Seeds of particular interest include the oil seeds, such as from Arabidopsis, Brassica, cotton, soybean, safflower, sunflower, tobacco, flax, peanut, or the like. Seeds of species such as wheat, maize, or rice may also be of interest.

The nucleotide sequence that comprises the promoter of this invention contains more than 2000 nucleotides. Based on the analysis of other plant promoters it seems likely that a substantially smaller region of sequence contained within the promoter of this invention would exhibit similar properties. For instance, as noted above, a 152 bp fragment from the napin promoter directed strong expression of the β-glucuronidase reporter gene in *B. napus* and tobacco seeds (Stalberg et al., 1996). Thus, we envision that a subsequence of a few hundred nucleotides or less may be found to have the same or similar properties as the full sequence disclosed here.

This subsequence may be identified by the kinds of experiments exemplified in the work of Stalberg et al. (1996) and others, such as those cited in the review by Bevan et al. (1993). The minimal promoter sequence can be identified by successively removing nucleotides from the promoter sequence (i.e. truncation) and comparing the activity of the modified promoter with that of the native promoter. In addition, linker scanning or saturation mutagenesis may be used to produce the modified promoter. The promoter activity that may be assayed include, for example, the amount of transcription, the temporal specificity of transcription (i.e., early), the spatial specificity of transcription (i.e., seed), or a combination thereof of the kappa hydroxylase promoter. In a similar manner, enhancer or silencer sequences may be identified and modified. An enhancer or silencer sequence would not determine the position of transcription initiation, but could function in either orientation relative to the promoter and could be located at some distance from the promoter; an enhancer would increase transcription from an operably linked promoter and a silencer would decrease transcription from an operably linked promoter, presumably due to the presence of a cognate binding factor that recognizes the enhancer or silencer sequence. An enhancer binding factor would be expected to be present in early seed tissues whereas a silencer binding factor would be expected to be present in tissues other than seed or at times other than early development. The promoter, enhancer, silencer, or a combination thereof may be responsible for early seed-specific transcription by the kappa hydroxylase regulatory region. The promoter, enhancer, and/or silencer modules identified by genetic manipulation may be combined with native sequences or heterologous regulatory sequence from other genes, preferably plant genes.

Computer comparison of 5' untranslated regions that are conserved between different plant fatty acyl hydroxylase genes may also be used to identify transcription regulatory regions (Gribskov and Devereux, 1991). Regulatory regions may also be identified by searching for consensus sequences that would be recognized by a known transcription binding factor, often such consensus sequences will exhibit dyad symmetry. The function of such putative regulatory regions may be confirmed by gel retardation or nuclease protection.

An assay for identifying a transcription regulatory region will typically involve fusing the region to a suitable reporter gene, such as the *E. coli* β-glucuronidase, then introducing that reporter construct into transgenic plants and assaying the amount of β-glucuronidase activity, protein, or mRNA produced (see Gallagher, 1992). Other reporter genes may be used, for example, alkaline phosphatase, chloramphenicol acetyltransferase, luciferase, β-galactosidase, green fluorescent protein, or derivatives thereof. Preferably, the assays are performed on stably transformed plants, but useful information may sometimes be gained by assaying tissues which have been transiently transformed with the constructs by particle bombardment or the like. Thus, many derivatives of the regulatory region disclosed herein are envisioned which would have similar or equal levels of activity. In addition, it is envisioned that many nucleotide changes in the sequence of the transcription regulatory region or a derivative, will have equivalent activity. Thus, deletions, insertions, inversions, and/or substitutions in the disclosed nucleotide sequence may produce derivatives of the regulatory region with similar biological activity (e.g., amount of transcription, early transcription, seed-specific transcription). Preferably, a functionally equivalent derivative of SEQ ID NO:1 would comprise at least 2000 bp, at least 1600 bp, at least 1400 bp, at least 1200 bp, at least 1000 bp, at least 800 bp, at least 600 bp, at least 400 bp, at least 200 bp, at least 100 bp, or at least 50 bp.

The following examples are offered by way of illustration and not by way of limitation.

EXAMPLES

Abbreviations: X-Gluc (5-bromo-4-chloro-3-indolyl-β-D-glucuronic acid) and GUS (β-glucuronidase).

MATERIALS AND METHODS
Cloning Vectors

Figure 2:
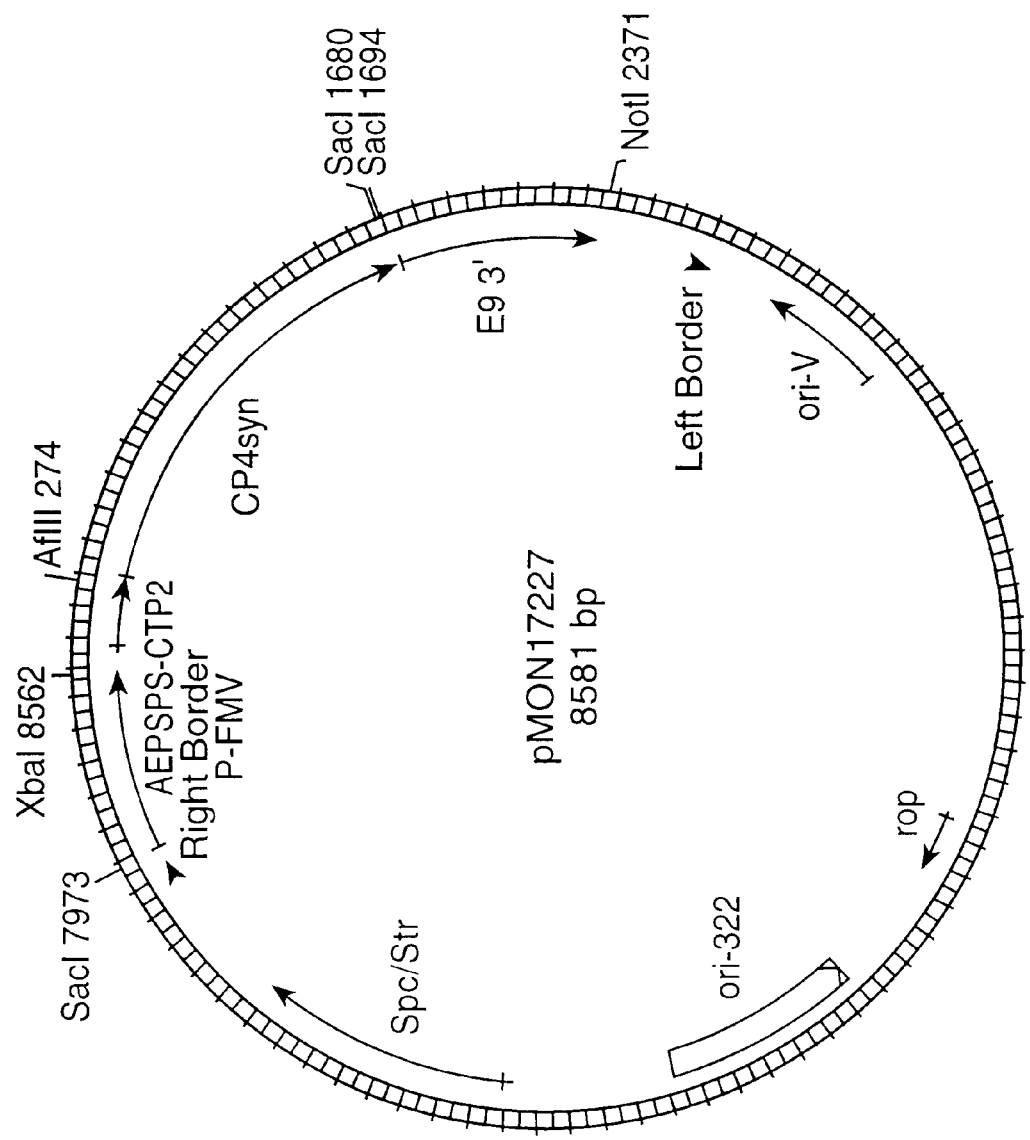
FIG. 2 is a restriction map of plasmid pMON17227.

The binary Ti plasmid pBI121 was purchased from Clontech (Palo Alto, Calif.). The ColE1-derived vector pMON26112 was obtained from Monsanto and is shown in FIG. 1. This plasmid, which contains the napin promoter from *Brassica napus*, replicates in *E. coli* where it confers ampicillin resistance. The binary Ti plasmid pMON17227 (FIG. 2) contains an origin of replication from pBR322 to permit replication in *E. coli*, a spectinomycin/streptomycin resistance gene for selection in bacterial hosts and the left and right borders of the Ti plasmid flanking the CP4 synthase gene for selection on glyphosate and a NotI cloning site upstream of the nopaline synthase gene terminator sequence. The plasmid pMON17227-pLesq-GUS is a binary Ti plasmid derived from pMON17227 as described below.

Measurement of GUS Activity

The protocol for detecting GUS activity was as follows. Tissues were incubated in staining buffer (50 mM $KPO_4$ buffer pH 7.0 containing 20% methanol, 0.5% Triton X-100, 1 mM potassium ferrocyanide, 1 mM potassium ferricyanide and 3 mM X-Gluc). Typically, the tissue was incubated in this solution for about 12 hours but, in some cases where the staining was strong, the tissue was removed sooner and staining was completed in a shorter time. Samples were placed in a vacuum chamber at 650 mm Hg for 2 min then incubated for 15 hours at 37° C. Following staining, samples were cleared by successive 5 min immersions in 20%, 40%, 60% and 70% ethanol.

GUS activity was quantitated visually as follows: non-activity was scored as 0, the highest level of GUS activity observed was scored as 4 with a quasi-logarithmic scale. Samples that were approximately 50% as darkly stained as those given a rating of 4, were rated as 3; samples that were approximately 50% as darkly stained as those given a rating of 4, were rated as 3; samples that were approximately 50% as darkly stained as those given a rating of 3, were rated as 2; and samples that were approximately 50% as darkly stained as those given a rating of 2, were rated as 1.

EXAMPLE 1

Seed-Specific Expression Of Foreign Genes In Transgenic Arabidopsis Thaliana

Isolation of a Seed-Specific Promoter from *L. fendleri*

Genomic DNA was prepared from young leaves of *L. fendleri* as described by Murray and Thompson (1980). A Sau3AI-partial digest genomic library constructed in the vector λDashII (Stratagene, La Jolla, Calif.) was prepared by partially digesting 500 μg of DNA, size selecting the DNA on a sucrose gradient (Sambrook et al., 1989), and ligating the DNA (12 kb average size) to the BamHI-digested arms of XDashII. The entire ligation was packaged according to the manufacturer's conditions and plated on *E. coli* strain XL1-Blue MRA-P2 (Stratagene). This yielded $5 \times 10^5$ primary recombinant clones. The library was then amplified according to the manufacturer's instructions. A fraction of the genomic library was plated on *E. coli* XL1-Blue and resulting plaques (150,000) were lifted to charged nylon membranes (Hybond $N^+$, Amersham, Arlington Heights, Ill.), according to the manufacturer's recommendations. DNA was crosslinked to the filters under UV with a Stratalinker (Stratagene).

Several clones carrying genomic sequences corresponding to the *L. fendleri* hydroxylase were isolated by probing the membranes with a cDNA clone of the *L. fendleri* kappa hydroxylase carried on plasmid pLesq2 (described in U.S. pat. appln. Ser. No. 08/530,862). The insert from plasmid pLesq2 was labeled with $^{32}p$ by random priming. The filters were prehybridized for 2 hours at 65° C. in 7% SDS, 1 mM EDTA, 0.25 M $Na_2HPO_4$ (pH 7.2), 1% BSA and hybridized to the probe for 16 hours in the same solution. The filters were sequentially washed at 65° C. in solutions containing 2× SSC, 1× SSC, 0.5× SSC in addition to 0.1 % SDS. A 4.5 kb HindIII/NotI fragment containing the complete coding sequence for the hydroxylase and approximately 2.2 kb of the 5' upstream region was subcloned into the corresponding sites of pBluescript KS (Stratagene) to produce plasmid pLesqtot, and the sequence of the promoter region determined completely using an automatic sequencer by the dideoxy chain termination method. Sequence data was analyzed using the computer software package DNASIS (Hitachi, Brisbane, Calif.).

Partial sequence of the insert in clone pLesqtot is shown in FIG. 3 (SEQ ID NO:1). The sequence comprises 3670 bp of continuous DNA sequence. The clone encodes a 2217 bp untranslated region (i.e., nucleotides preceding the first ATG codon), an 1152 bp open reading frame, and a 302 bp 3' untranslated region. The open reading frame encodes a 384 amino acid protein with a predicted molecular weight of 44,370.

Construction of the Vector pBI101-pLesq-GUS and Transformation of Arabidopsis

Figure 4:
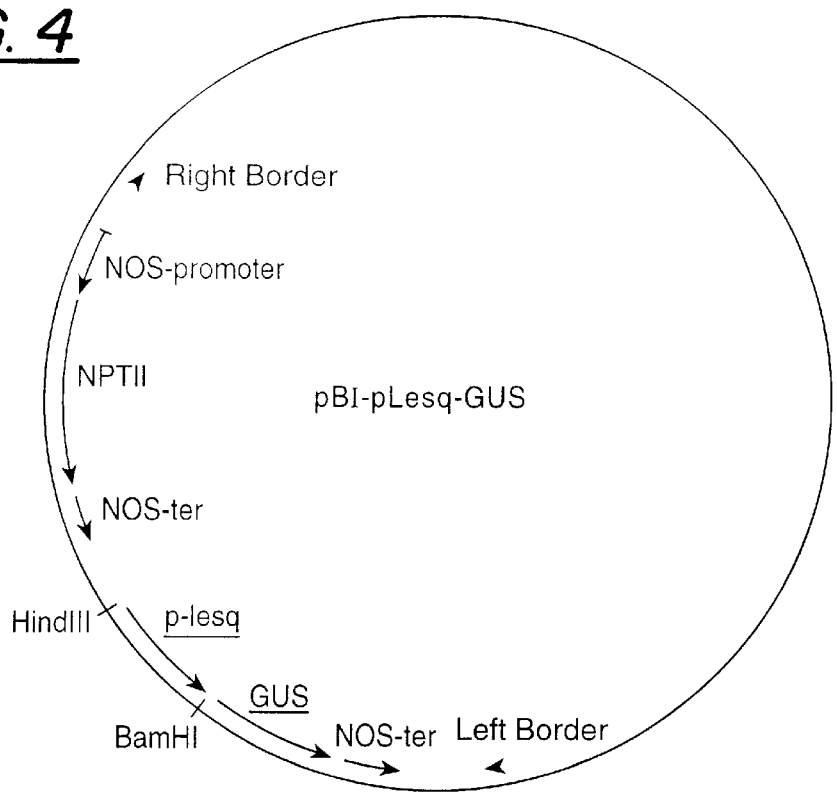
FIG. 4 is a restriction map of plasmid pBI-pLesq-GUS.

In a first step, pLesqtot was cut with HindIII and EcoRI, and a 2.2 kb insert fragment was cloned into pBluescript KS. The resulting vector, pLesqprom, contains 2.2 kb of sequence upstream of the ORF in pLesqtot. The promoter fragment did not contain a BamHI site but the polylinker of pBluescipt KS contains a BamHI site adjacent to the EcoRI cloning site. Thus, pLesqprom was then cut with HindIII and BamHI and the insert fragment purified by agarose gel electrophoresis. pBI121 was cut with the same enzymes to release the 35S promoter fragment. The HindIII/BamHI insert fragment of pLesqprom was then ligated into the corresponding sites of pBI121 to obtain the vector pBI-pLesq-GUS (FIG. 4). pBI-pLesq-GUS was then introduced into Agrobacterium tumefaciens strain GV3101 by electroporation, and used to transform Arabidopsis plants.

Cells for electroporation were prepared as follows. GV3101 was grown in LB medium (10 g tryptone, 5 g yeast extract, 5 g NaCl per liter of water). A 250 ml culture was grown to $OD_{600=0.6}$, then centrifuged at 4000 rpm (Sorvall GS-A rotor) for 15 min. The supernatant was aspirated immediately from the loose pellet, which was gently resuspended in 500 ml ice-cold water. The cells were centrifuged as before, resuspended in 30 ml ice-cold water, transferred to a 30 ml tube, and centrifuged at 5000 rpm (Sorvall SS-34 rotor) for 5 min. This was repeated three times, resuspending the cells consecutively in 30 ml ice-cold water, 30 ml ice-cold 10% glycerol, and finally in 0.75 ml ice-cold 10% glycerol. These cells were aliquoted, frozen in liquid nitrogen, and stored at −80° C.

Electroporation employed a GenePulser instrument (Bio-Rad, Hercules, Calif.) using cold 2 mm-gap cuvettes containing 40 μl of cells and 1 μl of DNA in water, at a voltage of 2.5 KV and capacitance of 25 μF. The electroporated cells were diluted with 1 ml SOC medium (Sambrook et al., 1989, page A2) and incubated at 28° C. for 2–4 hours before plating on LB medium containing kanamycin (50 mg/l).

Arabidopsis plants were transformed by the in planta transformation procedure essentially as described by Bechtold et al. (1993). Cells of A. tumefaciens GV3101(pBI-pLesq-GUS) were harvested from liquid cultures by centrifugation, then resuspended in infiltration medium at $OD_{600=0.8}$. Infiltration medium was Murashige and Skoog macro and micronutrient medium (Sigma, St. Louis, Mo.) containing 10 mg/l 6-benzylaminopurine and 5% glucose. Batches of 12–15 plants were grown for 3 to 4 weeks in natural light at a mean daily temperature of approximately 25° C. in 3.5 inch pots containing soil. The intact plants were immersed in the bacterial suspension, then transferred to a vacuum chamber and placed under 600 mm of vacuum produced by a laboratory vacuum pump until tissues appeared uniformly water-soaked (approximately 10 min). The plants were grown at 25° C. under continuous light (100 $\mu$mol m$^{-2}$ S−1 irradiation in the 400 to 700 nm range) for four weeks. The seeds obtained from all the plants in a pot were harvested as one batch. The seeds were sterilized by sequential treatment for 2 min with ethanol followed by 10 min in a mixture of household bleach (Chlorox), water and Tween-80 (50%, 50%, and 0.05%), then rinsed thoroughly with sterile water. The seeds were plated at high density (2000 to 4000 per plate) onto agar-solidified medium in 100 mm petri plates containing ½× Murashige and Skoog salts medium enriched with B5 vitamins (Sigma) and containing kanamycin at 50 mg/l. After incubation for 48 hours at 4° C. to stimulate germination, seedlings were grown for a period of seven days until transformants were clearly identifiable as healthy green seedlings against a background of chlorotic kanamycin-sensitive seedlings. The transformants were transferred to soil and grown to maturity. More than 20 transformants were obtained.

Analysis of Transgenic Plants

The activity of the kappa hydroxylase promoter was assayed by staining various tissues of the transgenic Arabidopsis plants for the presence of β-glucuronidase activity by staining with X-Gluc (5-bromo-4-chloro-3-indolyl-β-D-glucuronic acid). Histochemical staining was carried out on leaves, stems, siliques, flowers and developing embryos isolated at different stages from transgenic Arabidopsis plants. Arabidopsis embryos from three transgenic plants were dissected out of their seedcoat, and staged from late-heart stage to late-cotyledon stage on plates containing MS-salts medium with 7.5 g/l agar, before being transferred to GUS staining buffer. Leaves, stems, and inflorescences were collected from transgenic plants and directly immersed in staining buffer.

The results obtained with three independent transgenic plants, designated 1 to 3, is shown in Table 1. It can be seen from these results that the kappa hydroxylase promoter caused the appearance of GUS activity as early as the torpedo stage embryo. The GUS activity persisted throughout subsequent development of the embryo. The amount of GUS activity in pBI-pLesq-GUS transgenic plants was compared with transgenic plants expressing the GUS gene driven by the promoter from the gene encoding the alpha subunit of the soybean beta-conglycinin (7S) gene (Hirai et al., 1994). p7S-GUS plants were chosen for their high level of GUS expression. The Lesquerella promoter was active earlier than the 7S promoter. Onset of activity coincides with that of storage lipid accumulation in Arabidopsis (Table 1). The level of GUS activity in the transgenic plants containing the kappa hydroxlase promoter was at least as high as in the transgenc plants containing the soybean β-conglycinin promoter. There was no GUS activity in samples of leaves, stems, or pods of the transgenic plants. Thus, the kappa hydroxylase promoter can be used to cause seed-specific expression of foreign genes in transgenic plants.

TABLE 1

Histochemical staining of transgenic Arabidopsis plants expressing the GUS gene under the control of different seed-specific promoters

| | A | B | C | E1 | E2 | E3 | E4 | E5 | F |
|---|---|---|---|---|---|---|---|---|---|
| Lesquerella kappa hydroxylase promoter | | | | | | | | | |
| 1 | 0 | 0 | 0 | 0 | 1 | 2 | 4 | 4 | 1 |
| 2 | 0 | 0 | 0 | 0 | 1 | 2 | 4 | 4 | 1 |
| 3 | 0 | 0 | 0 | 0 | 1 | 2 | 4 | 4 | 1 |
| Soybean beta-conglycinin promoter (alpha subunit) | | | | | | | | | |
| 1 | 0 | 0 | 0 | 0 | 0 | 0 | 2 | 4 | 0 |
| 2 | 0 | 0 | 0 | 0 | 0 | 0 | 2 | 4 | 0 |
| 3 | 0 | 0 | 0 | 0 | 0 | 0 | 2 | 4 | 0 |

A: leaf
B: stem
C: pod
E1: embryo (heart stage)
E2: embryo (torpedo stage)
E3: embryo (cane-shaped embryo)
E4: embryo (early cotyledon stage)
E5: mature embryo
0: no detectable staining
4: highest intensity of staining detected among samples of the same tissue type
3: intensity of staining about ½ of the maximum intensity
2: intensity of staining about ¼ of the maximum intensity
1: light staining, about 1/10 of the maximum intensity

EXAMPLE 2

Seed-Specifc Expression Of Foreign Genes In Transgenic Brassica Napus

Construction of the Vector pMON17227-pLesq-GUS for Transformation of Canola

Figure 5:
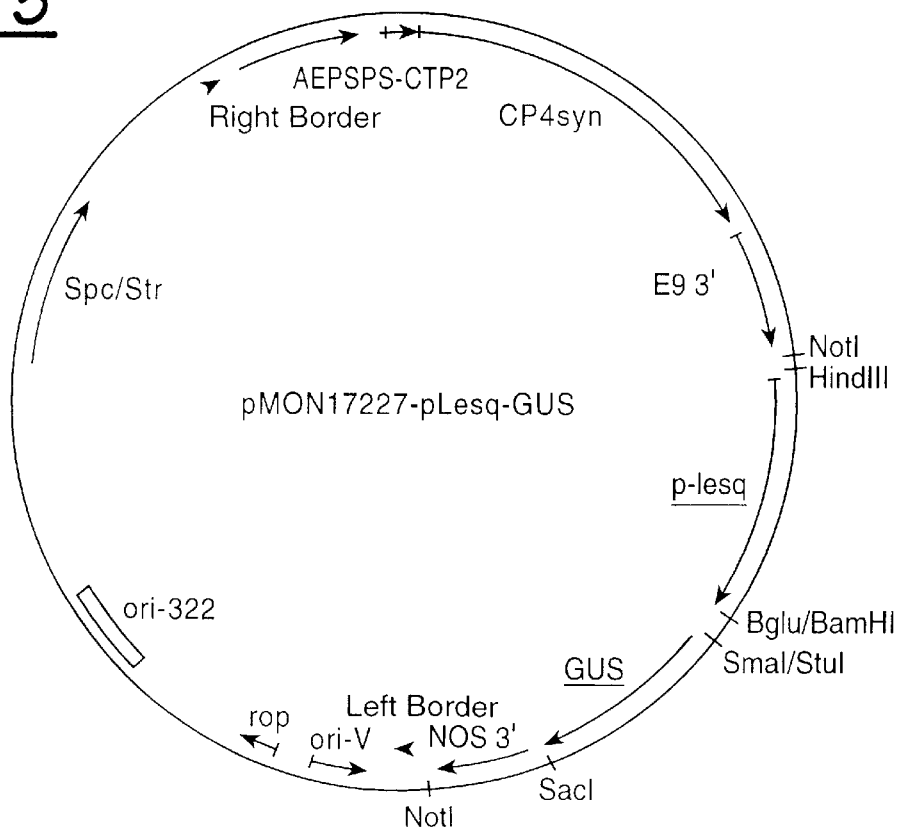
FIG. 5 is a restriction map of pMON17227-pLesq-GUS.

In a first step, the GUS gene was purified by cutting the vector pBI121 (Clontech) with SmaI and SacI. The insert fragment containing the GUS gene was cloned into the StuI and SacI sites of vector pMON26112, resulting in the vector pMON26112-GUS. In a second step, a HindIII/BamHI fragment from pLesqprom containing the L. fendleri kappa hydroxylase promoter was cloned into pMON26112-GUS cut with HindIII and BglII. The resulting vector (pMON26112-pLesq-GUS) was cut with NotI, and the insert fragment ligated to the vector pMON17227 cut with NotI. The final vector, pMON17227-pLesq-GUS (FIG. 5) was used to introduce the Lesquerella promoter-GUS cassette into canola plants using Agrobacterium-mediated transformation.

Transformation and Regeneration of B. napus

Agrobacterium strain ABI containing pMON17227-pLesq-GUS was used to transform Brassica napus cv Westar essentially as described by Fry et al. (1987). Briefly, seedlings are planted in Metro Mix 350 and grown in a growth chamber with these conditions: temperature day 15° C. and night 10° C., light intensity 600 $\mu$mol m$^{-2}$s$^{-1}$, 8 hours night, relative humidity 50%, and are transferred into 6 inch pots when they are 3 weeks old. Five-week-old Westar plants are harvested once the plants bolt, but prior to flowering (plants with up to 3 flowers may be harvested). The leaves and buds are removed and the 4–5 inches of stem below the flower buds are used as the explant tissue source. Just prior to inoculation, the stems are sterilized as follows: soak in 70% ethanol for 1 minute, soak in 38% Clorox for 20 minutes, rinse two times in sterile deionized water, and soak in two tablespoons of Captan 50-WP (ICI) plus 500 ml sterile water for 15 minutes.

Aqrobacterium Preparation

Agrobacterium is streaked onto an LB plate containing spectinomycin 100 mg/l, Streptomycin 100 mg/l, chloramphenicol 25 mg/l, and kanamycin 50 mg/l (denoted LB-SSCK). Two days before inoculation, a 10 $\mu$l loop of Agrobacterium is placed into a tube containing 2 mls of LB-SSCK and put onto a rotator to grow overnight. The day before inoculation, the Agrobacterium is subcultured, 200 $\mu$l is placed in 2 ml of fresh LB-SSCK and returned to the rotator to grow overnight. On the inoculation day, the Agrobacterium is diluted 1:10 with MS liquid medium. An $OD_{600}$ reading is taken, readings in the range of 0.2 to 0.4 are acceptable.

Explant Inoculation

Stems are cut into one quarter inch segments, noting the basal orientation of the stems. Explants are inoculated in a petri plate for 5 minutes with the 1:10 dilution of Agrobacterium; 5 ml Agrobacterium per 5 stems are used and the Agrobacterium is pipetted directly on top of the explants. Agrobacterium is aspirated off of the explants after the 5 minute inoculation time. Stem explants are cultured in the basal-side down orientation for an optimal shoot regeneration response on the co-culture plates, (1/10 MS medium with a 2 ml TXD liquid medium covered with sterile 8.5 cm filter paper). TXD medium contains 4.3 g Gibco MS medium, 2 ml of 500×solution of Gamborg B5 mixture (Sigma), 8 ml p-chloro-phenoxyacetic acid (0.5 mg/ml) 0.01 ml Kinetin (0.5 mg/ml), 30 g sucrose and water to one liter. Co-culture plates are put in clear plastic bags which are slit and placed at 25° C., 24 hours continuous cool-white light.

Tissue Selection and Regeneration

After a 2 day co-culture period, stem explants are moved onto MS medium containing 500 mg/l ticarcillin, 50 mg/l cefotaxime, and 1 mg/l benzylaminopurine (BAP) for a 3 day delay period; again plates are put in clear plastic bags which are slit and placed at 25° C., 24 hours continuous cool-white light. After a three-day delay period, stem explants are moved onto MS 0.1 mM glyphosate selection medium containing glyphosate and the abovementioned levels of ticarcillin, cefotaxime, and BAP for three weeks. Then, the stem explants are moved onto the MS 0.1 mM glyphosate selection medium containing the same amounts of ticarcillin, cefotaxime, and BAP cited above plus 0.5 mg/l gibberellin ($GA_3$) which was found to enhance shoot elongation, for another three week period. After these six weeks on glyphosate selection medium, green, normal developing shoots are excised from the stem explants. Shoots (4–5 shoots per plate) are placed in rooting medium [Gibco MS salts, vitamins, 3% sucrose containing the above levels of ticarcillin and cefotaxime and 2 mg/l indolebutyric acid (IBA)]. Root development begins to occur as early as one week after shoots go onto rooting medium. At the 2 week timepoint, shoots with a large root base are moved into 2 ½ inch pots with potting soil (Metro Mix 350); flats are covered with the clear plastic domes so the shoots can elongate. All plants are placed in a growth chamber with the same conditions as described above for stock plant growth. When shoots are hardened off after 3–4 days, the plastic domes are cracked and several days later removed completely. The plants are grown in a growth chamber at 22° C. in a 16 hr/8 hr light/dark cycle with light intensity 220 $\mu$E m$^2$ S$^{-1}$ and after several weeks are transferred to the greenhouse.

Analysis of Transgenic Plants

Eighteen regenerated B. napus plants were examined for embyro-specific expression of the GUS gene using the same scale for expression levels as described in Example 1.

Transgenic canola pods and seeds were collected at less than 10, 10, 16, 21, 28, 35 dpa and at maturity. Leaf, stem, pods and seed samples were stained for β-glucuronidase activity as described above. The results of the GUS assays are presented in Table 2.

TABLE 2

Histochemical staining of transgenic *B. napus* plants expressing the GUS gene under the control of different seed-specific promoters

| | | | | | Stage | | | | |
|---|---|---|---|---|---|---|---|---|---|
| A | B | C | D1 | D2 | D3 | D4 | D5 | D6 | D7 |
| 1 | 0 | 0 | 0 | | | | | 1 | 1 |
| 2 | 0 | 0 | 0 | 3–4 | 3–4 | | | 2 | 0 |
| 3 | 0 | 0 | 0 | 3–4 | 3–4 | | | 1 | 1 |
| 4 | 0 | 0 | 0 | 3–4 | 3–4 | 3–4 | 3–4 | 1 | 0 |
| 5 | 0 | 0 | 0 | 3–4 | 3–4 | | | 1 | 1 |
| 6 | 0 | 0 | | | | | | 1 | 0 |
| 7 | 0 | 0 | 0 | 3–4 | 3–4 | | | 1 | 0 |
| 8 | 0 | 0 | 0 | 3–4 | 3–4 | 3–4 | 3–4 | 3–4 | |
| 9 | 0 | 0 | 0 | 1 | 2 | | | 1 | 0 |
| 10 | 0 | 0 | 0 | 2 | 2 | 2 | | | |
| 11 | 0 | 0 | 0 | 2 | 3–4 | | | | |
| 12 | 0 | 0 | 0 | 3–4 | 3–4 | | | | |
| 13 | 0 | 0 | 0 | 3–4 | 3–4 | 3–4 | 3–4 | 4 | 2 | 1 |
| 14 | 0 | 0 | | 3–4 | | | | | |
| 15 | 0 | 0 | 0 | | 3–4 | | | | |
| 16 | 0 | 0 | 0 | 3–4 | 3–4 | | | | |
| 17 | 0 | 0 | 0 | 3–4 | 3–4 | | | | |
| 18 | 0 | 0 | 0 | 3–4 | 3–4 | | | | |

A: leaf
B: stem
C: pod
D1: seed 16 dpa
D2: seed 21 dpa
D3: seed 28 dpa
D4: seed 35 dpa
D5: mature seed
D6: seed: <10 dpa
D7: seed: 10 dpa It is apparent from the results in Table 2 that a foreign gene fused to the kappa hydroxylase promoter is not expressed at significant levels in non-seed tissues, but is abundantly expressed in developing seeds. High levels of GUS staining were apparent as early as 16 days post-anthesis and the staining persisted throughout seed development. Thus, the kappa hydroxylase promoter is a useful promoter for causing the expression of foreign genes in plants. The promoter is particularly useful in applications where it is desirable to have the gene of interest transcribed at high levels an early stage of seed development and persist throughout seed development. Such applications include modification of seed lipid metabolism.

All publications and patent applications mentioned in this specification are indicative of the level of skill of those skilled in the art to which this invention pertains.

All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious to the skilled artisan that certain changes and modifications may be practiced within the scope of the appended claims.

REFERENCES

Bechtold, N., Ellis, J., Pelletier, G. (1993) In planta Agrobacterium-mediated gene transfer by infiltration of adult *Arabidopsis thaliana* plants. C.R. Acad. Sci. Paris 316, 1194–1199.

Bevan, M., Colot, V., Hammond-Kossack, M., Holdsworth, M., Torres de Zabala, M., Smith, C., Grierson, C., Beggs, K. (1993) Transcriptional control of plant storage protein genes. Phil. Trans. Royal Soc. Lond. Biol. Sci. 342, 209–215.

Chen, Z. L., Pan, N. S., Beachy, R.N. (1988) A DNA sequence element that confers seed-specific enhancement to a constitutive promoter. EMBO J. 6, 3559–3564.

Fraley, R., Rogers, S., Horsch, R. B. (1986) Genetic transformation in higher plants. Crit. Rev. Plant Sci. 4, 1–46.

Fry et al., (1987) Transformation of *Brassica napus* with *Agrobacterium tumefaciens* based vectors. Plant Cell Reports 6, 321–325.

Gallagher, S. R. (1992) *GUS Protocols*. Academic Press, San Diego.

Gribskov, M., Devereux, J. (1991) *Sequence Analysis Primer*. Stockton Press, New York.

Hirai, M. Y., Fujiwara, T., Goto, K., Komeda, Y., Chino, M., Naito, S. (1994) Differential regulation of soybean seed storage protein gene promoter-GUS fusions by exogenously applied methionine in transgenic *Arabidopsis thaliana*. Plant Cell Physiology 35, 927–934.

Lindsey, K. (1996) Plant transformation systems. In Transgenic Plants: *A Production System for Industrial and Pharmaceutical Proteins*. Owen, M.R.L., Pen, J. (Eds.) Wiley, New York, pp. 5–25.

Murray, M. G., Thompson, W. F. (1980) Rapid isolation of high molecular weight plant DNA. Nucl. Acids Res. 8, 4321–4325.

Post-Beittenmiller, D., Ohlrogge, J., Somerville, C. R. (1992) Regulation of plant lipid biosynthesis: An example of developmental regulation superimposed on a ubiquitous pathway. *In Control of Plant Gene Expression*. Verma, D. P. (Ed.) Telford Press, pp. 157–174.

Sambrook, J., Fritsch, E. F., Maniatis, T. (1989) *Molecular Cloning: A Laboratory Manual*, 2nd Ed., Cold Spring Harbor Laboratory Press.

Stalberg, K., Ellerstoem, M., Ezcurra, I., Ablov, S., Rask, L. (1996) Disruption of an overlapping E-box-ABRE motif abolished high transcription of the napA storage-protein promoter in transgenic *Brassica napus* seeds. Planta 199, 515–519.

Voelker, T. A., Hayes, T. R, Cranmer, A. M., Turner, J. C., Davies, H. M (1996) Genetic engineering of a quantitative trait: Metabolic and genetic parameters influencing the accumulation of laurate in rapeseed. Plant Journal 9, 229–241.

We claim:

1. An isolated nucleic acid comprised of a transcription regulatory region said transcriptional regulatory region comprising nucleotide 1 to nucleotide 2214 of SEQ ID NO:1.

2. The nucleic acid according to claim 1 further comprised of a coding sequence for a plant kappa hydroxylase gene.

3. A recombinant nucleic acid comprised of the nucleic acid according to claim 1 and a heterologous gene.

4. The recombinant nucleic acid according to claim 3 wherein the heterologous gene is an enzyme of lipid metabolism.

5. The recombinant nucleic acid according to claim 3 wherein the heterologous gene is a plant hydroxylase gene.

6. A host plant cell comprising the recombinant nucleic acid according to claim 3.

7. An expression construct comprised of a transcription regulatory region from claim 3 and a transcription termination region.

8. The expression construct according to claim 7 wherein the transcription regulatory region is from a *Lesquerella fendleri* kappa hydroxylase gene.

9. The expression construct according to claim 7 further comprised of a translation initiation region and a translation termination region.

10. The expression construct according to claim 7 further comprised of a coding sequence for a plant kappa hydroxylase gene.

11. The expression construct according to claim 7 further comprised of a coding sequence for a heterologous gene.

12. The expression construct according to claim 11 wherein the heterologous gene is an enzyme of lipid metabolism.

13. The expression construct according to claim 11 wherein the heterologous gene is operably linked to the transcription regulatory region and the transcription termination region such that a sense transcript of the heterologous gene would be produced.

14. The expression construct according to claim 7 wherein the transcription regulatory region is a promoter.

15. A microbial or a plant cell comprised of the expression construct according to claim 7.

16. The host cell according to claim 15 wherein the host cell is a host plant cell.

17. A host plant cell comprised of the expression construct according to claim 11.

18. The host plant cell according to claim 17 wherein host plant cell is a Brassica species.

19. The host plant cell according to claim 17 wherein the host plant cell is a dicotyledenous species.

20. A process of altering fatty acid composition of a ed comprising:
 (a) transforming a host plant cell with the recombinant nucleic acid according to claim 4,
 (b) obtaining a seed from a collection of transformed host plant cells, and
 (c) screening the seeds for a desired composition of fatty acid.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 3670 nucleotides
        (B) TYPE: nucleic acid
        (C) STRANDEDNESS: single
        (D) TOPOLOGY: linear (xi) SEQUENCE DESCRIPTION: SEQ ID NO:1:

```
AAGCTTTTGA GCTCATCAGT TACTCAGGAA GATTAAGTCT                    40
TTGCTTGTTG TCTGATTTTC TTTAAATACA TGAAGGATCG                    80
GTTATGAATC TTCTTTTTTT GTGTTTTGGG ATTATGAAGC                   120
TGTCTTTGGA TATTAGTTGC GGTTATTAGC ATGCTTCTCT                   160
TTTGTGTTTT GGGGATTATG AAGCAGGGTC TGTCTATGTA                   200
ATGCATTTTG TTTGAAAACT CAGCTAATGC TAATGCAATT                   240
TCTTTTGAAA CCTTTGTTAT GTTTTCGAAA ATATTGAATA                   280
NGTTCTGTTA TGGATTTATT TGCAAAAGCC ATTGATTAAA                   320
TCAAACATTA CATAAGAACA ACATTCATTA TTAACTAATT                   360
AGAGATGCAA ACACAACAT  TACATACAAC ATCAGTGACT                   400
AATTATTGAG ACAAAACAAC ATCACATACA CAAACATTCA                   440
TCTCATACAT CACTTAGAGA GACACAAAAA GCAACCAAAC                   480
ACAACTATTC CGGCAACAAC AATTAGCTTC ATACGTTTTG                   520
CTTCTCCTTT CAAGCCTTCA ATCATCTTCT CACAGCCACG                   560
AATCTGAGCC TTCAATAATA ACATTTCTTC ATCGTGACAC                   600
TTCTCACGGT TATGAATGTA AGCCTTTATG TCCTCTACTT                   640
CTTCTACTAA AGACACATCA GTCCACTTCC AGGTGTGGAA                   680
TCCTCCTCTT TTGAAATTTT TCTCACAGGT ATGGAATAAT                   720
CTACCTAGGT TTTTTGGAGT TCTTGAGGTT CTGATCACAA                   760
CACGACATCC AAATCGACAG GTCTTAGGAA AACCACGATG                   800
GTTATCATCT TCAAGCTCAC TGTCAAAAGA GAAAAACGAG                   840
TTTGAAGAAG AAGAAGGCAT TATCAATTTC AGAGAATTTT                   880
GGAGAATTTT GAGAGATTGA GAATTGGGAA ATAAGAACCC                   920
TAATCCCCAA TTTATGAGAT TGAAAATATA TCCGTTAGAG                   960
AAGAAACATA ATGCTGTGCG TTTTAATTAG AAAAAATAGA                  1000
GATGGGCTTT ATCTTTTGTT AAGAGTTTTG GGCTTGGGCT                  1040
TGGGTTTTTG ATAAAAAAAT TTAATTAAAC CAAAACGACG                  1080
TCGTTTGGTT TAATTGTTGT TAAAAAAAAT TAAAACACCA                  1120
AAACGACGTC GTTTTGGTGT TATTAACGGC CTTAAAACGG                  1160
ATTAAATCCA TAATCCGTCA GTCAACTAGG TTACGGATGG                  1200
TCAACGGCGT TTTTGCATAA CGGAGGCACA GTTCAGGCTT                  1240
AACGGAGTGG ACCGAATGGC TTTTTAGGAA GTTTGTAACC                  1280
GGGATTTTTT GTTATGATG  TATTTGTCCC CGTCGGCTAT                  1320
TGTTTAGGCC GTTTTCCTA  TATATTGGAA ATAACTATTG                  1360
TCCAGACGAG TTACTTCTCC AACATATCAA GAAATGTTAC                  1400
```

```
AAAGAAGTGT TACAAAAATG TGTTACTAAG CCATAAAACT           1440

CAAAGCATAT ATCTTAGACC CTAAGCCTAA ACCCTAGAAC           1480

TTTCTAGGAC GTTTATACCT TGTCCTTTCT TTAGTTTCCT           1520

TTAAAGGCCT TCGTATTCAT AAGTTTTATT TTTGCTTAAT           1560

ACTAACACTA GAAATAATCA ACATAAACTA GGTTAAGTCG           1600

TGGATCTAAT TTTATTGTGA AAATGTAATT GCTTCTCTTA           1640

AGAAAGATT CATAGCAAAA TATTCGCATC TTTCTTGTGA            1680

ATCATCTTTT GTTTTTGGGG CTATTAAAGA AAAATTGAAC           1720

TCATGAAATG GTGACAACTT TATTCTAGAG GTAACAGAAC           1760

AAAAATATAG GAACAACACG TGTTGTTCAT AAACTACACG           1800

TATAATACTC AAGAAGATGA ATCTTTATAA GAATTTAGTT           1840

TTCTCATGAA AACATAAAAA ATTTTGTCAA TTGAAAGTGA           1880

CAGTTGAAGC AAAGGAACAA AAGGATGGTT GGTGATGATG           1920

CTGAAATGAA AATGTGTCAT TCATCAAATA CTAAATACTA           1960

CATTACTTGT CACTGCCTAC TTCTCCTATT TCCTCCGCCA           2000

CCCATTTTGG ACCCACGAGC CTTCCATTTA AACCCTCTCT          2040

CGTGCTATTC ACCAGAAGAG AAGCCAAGAG AGAGAGAGAG          2080

AGATTGTGCT GAGGATCATT GTCTTCTTCA TCGTTATTAA          2120

CGTAAGTTTT TTTTGACCAC TCATATCTAA AATCTAGTAC          2160

ATGCAATAGA TTAATGACTG TTCCTTCTTT TGATATTTTC          2200

AGCTTCTTGA ATTCAAGATG GGTGCTGGTG GAAGAATAAT          2240

GGTTACCCCC TCTTCCAAGA AATCAGAAAC TGAAGCCCTA          2280

AAACGTGGAC CATGTGAGAA ACCACCATTC ACTGTTAAAG          2320

ATCTGAAGAA AGCAATCCCA CAGCATTGTT TCAAGCGCTC          2360

TATCCCTCGT TCTTTCTCCT ACCTTCTCAC AGATATCACT          2400

TTAGTTTCTT GCTTCTACTA CGTTGCCACA AATTACTTCT          2440

CTCTTCTTCC TCAGCCTCTC TCTACTTACC TAGCTTGGCC          2480

TCTCTATTGG GTATGTCAAG GCTGTGTCTT AACCGGTATC          2520

TGGGTCATTG GCCATGAATG TGGTCACCAT GCATTCAGTG          2560

ACTATCAATG GGTAGATGAC ACTGTTGGTT TTATCTTCCA          2600

TTCCTTCCTT CTCGTCCCTT ACTTCTCCTG GAAATACAGT          2640

CATCGTCGTC ACCATTCCAA CAATGGATCT CTCGAGAAAG          2680

ATGAAGTCTT TGTCCCACCG AAAAAAGCTG CAGTCAAATG          2720

GTATGTTAAA TACCTCAACA ACCCTCTTGG ACGCATTCTG          2760

GTGTTAACAG TTCAGTTTAT CCTCGGGTGG CCTTTGTATC          2800

TAGCCTTTAA TGTATCAGGT AGACCTTATG ATGGTTTCGC          2840

TTCACATTTC TTCCCTCATG CACCTATCTT TAAAGACCGA          2880

GAACGCCTCC AGATATACAT CTCAGATGCT GGTATTCTAG          2920

CTGTCTGTTA TGGTCTTTAC CGTTACGCTG CTTCACAAGG          2960

ATTGACTGCT ATGATCTGCG TCTATGGAGT ACCGCTTTTG          3000
```

```
ATAGTGAACT TTTTCCTTGT CTTGGTAACT TTCTTGCAGC                3040

ACACTCATCC TTCGTTACCT CATTATGATT CAACCGAGTG                3080

GGAATGGATT AGAGGAGCTT TGGTTACGGT AGACAGAGAC                3120

TATGGAATAT TGAACAAGGT GTTCCATAAC ATAACAGACA                3160

CACATGTGGC TCATCATCTC TTTGCAACTA TACCGCATTA                3200

TAACGCAATG GAAGCTACAG AGGCGATAAA GCCAATACTT                3240

GGTGATTACT ACCACTTCGA TGGAACACCG TGGTATGTGG                3280

CCATGTATAG GGAAGCAAAG GAGTGTCTCT ATGTAGAACC                3320

GGATACGGAA CGTGGGAAGA AAGGTGTCTA CTATTACAAC                3360

AATAAGTTAT GAGGCTGATA GGGCGAGAGA AGTGCAATTA                3400

TCAATCTTTT TTTCATGTTT TAGGTGTCTT GTTTAAGAAG                3440

CTATGCTTTG TTTCAATAAT CTCAGAGTCC ATTTAGTTGT                3480

GTTCTGGTGC ATTTTGCCTA GTTATGTGGT GTCGGAAGTT                3520

AGTGTTCAAA CTGCTTCCTG CTGTGCTGCC CAGTGAAGAA                3560

CAAGTTTACG TGTTTAAAAT ACTCGGAACG AATTGACCAC                3600

AANATATCCA AAACCGGCTA TCCGAATTCC ATATCCGAAA                3640

ACCGGATATC CAAATTTCCA GAGTACTTAG                           3670
```